United States Patent
Osbrink et al.

(10) Patent No.: US 10,945,869 B2
(45) Date of Patent: Mar. 16, 2021

(54) LOW PROFILE STENT DELIVERY SYSTEM AND METHOD

(71) Applicant: Cook Medical Technologies LLC, Bloomington, IN (US)

(72) Inventors: Ruth Osbrink, Bloomington, IN (US); Ralf Spindler, Bloomington, IN (US)

(73) Assignee: Cook Medical Technologies, LLC, Bloomington, IN (US)

( * ) Notice: Subject to any disclaimer, the term of this patent is extended or adjusted under 35 U.S.C. 154(b) by 178 days.

(21) Appl. No.: 15/911,596

(22) Filed: Mar. 5, 2018

(65) Prior Publication Data
US 2018/0256376 A1   Sep. 13, 2018

Related U.S. Application Data

(60) Provisional application No. 62/468,999, filed on Mar. 9, 2017.

(51) Int. Cl.
*A61F 2/958* (2013.01)
*A61F 2/962* (2013.01)

(52) U.S. Cl.
CPC .............. *A61F 2/958* (2013.01); *A61F 2/962* (2013.01); *A61F 2002/9583* (2013.01)

(58) Field of Classification Search
CPC .. A61F 2/95; A61F 2/958; A61F 2/962; A61F 2/966; A61F 2002/9522; A61F 2002/9534; A61F 2002/9583
See application file for complete search history.

(56) References Cited

U.S. PATENT DOCUMENTS

| | | | |
|---|---|---|---|
| 5,545,135 | A | 8/1996 | Iacob et al. |
| 5,639,274 | A | 6/1997 | Fischell et al. |
| 5,989,280 | A | 11/1999 | Euteneuer et al. |
| 6,235,051 | B1 | 5/2001 | Murphy |
| 6,458,069 | B1 | 10/2002 | Tam et al. |
| 6,602,226 | B1 | 8/2003 | Smith et al. |
| 6,989,024 | B2 | 1/2006 | Hebert et al. |
| 7,056,336 | B2 | 6/2006 | Armstrong et al. |
| 7,160,318 | B2 | 1/2007 | Greenberg et al. |
| 7,175,652 | B2 | 2/2007 | Cook et al. |
| 7,232,459 | B2 | 6/2007 | Greenberg et al. |
| 7,294,146 | B2 | 11/2007 | Chew et al. |
| 7,413,573 | B2 | 8/2008 | Hartley et al. |
| 2002/0156496 | A1 | 10/2002 | Chermoni |
| 2004/0117004 | A1 | 6/2004 | Osborne et al. |
| 2004/0176833 | A1 | 9/2004 | Pavcnik et al. |
| 2004/0193179 | A1 | 9/2004 | Nikolchev |
| 2005/0159804 | A1 | 7/2005 | Lad et al. |
| 2006/0282152 | A1 | 12/2006 | Beyerlein et al. |

(Continued)

*Primary Examiner* — Melanie R Tyson
(74) *Attorney, Agent, or Firm* — Liell + McNeil

(57) ABSTRACT

A low profiled stent delivery system includes a balloon catheter with a balloon mounted at a first location, and a balloon expandable stent crimped about the balloon catheter at a second location. The stent expands from a crimped state to a less than fully expanded state responsive to movement of an auxiliary expander from a first configuration to a second configuration. An inner diameter of the stent in the less than fully expanded state is greater than an outer diameter of the balloon in a deflated state. After repositioning the balloon within the less than fully expanded state, the balloon is inflated to fully expand the stent.

15 Claims, 6 Drawing Sheets

(56) References Cited

U.S. PATENT DOCUMENTS

| | | | |
|---|---|---|---|
| 2007/0142858 A1* | 6/2007 | Bates | A61F 2/013 |
| | | | 606/200 |
| 2007/0282422 A1 | 12/2007 | Biggs et al. | |
| 2009/0048663 A1 | 2/2009 | Greenberg | |
| 2009/0125095 A1 | 5/2009 | Bui et al. | |
| 2009/0254166 A1* | 10/2009 | Chou | A61F 2/966 |
| | | | 623/1.11 |
| 2009/0312830 A1 | 12/2009 | McNulty et al. | |
| 2011/0295354 A1* | 12/2011 | Bueche | A61F 2/966 |
| | | | 623/1.11 |
| 2012/0245670 A1* | 9/2012 | Niwa | A61F 2/958 |
| | | | 623/1.11 |
| 2012/0310334 A1* | 12/2012 | Dolan | A61F 2/2433 |
| | | | 623/2.11 |

* cited by examiner

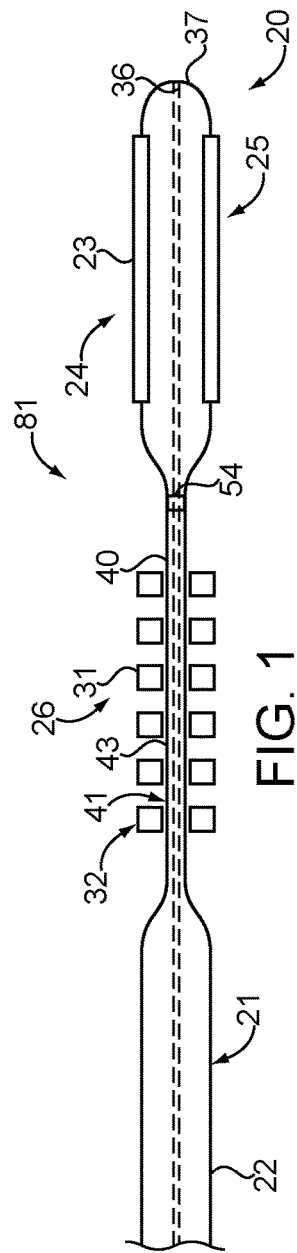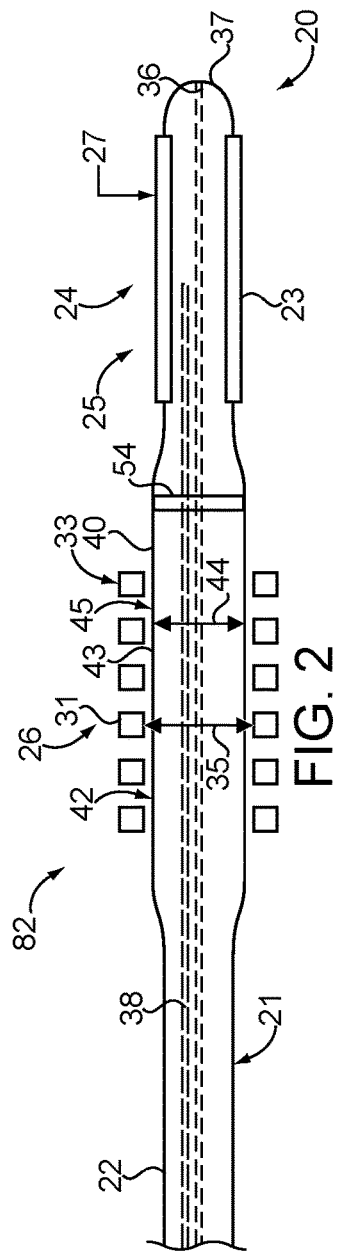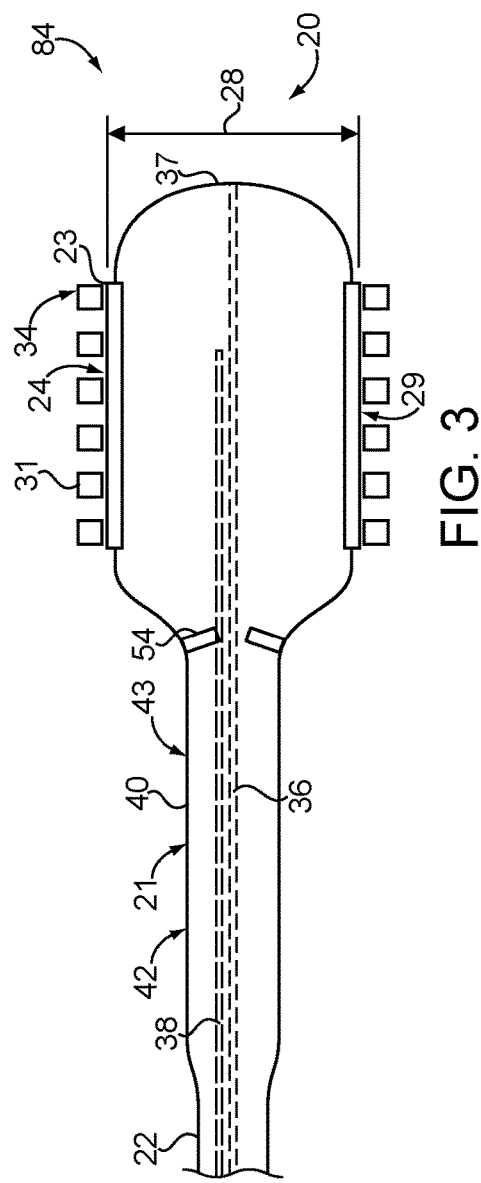

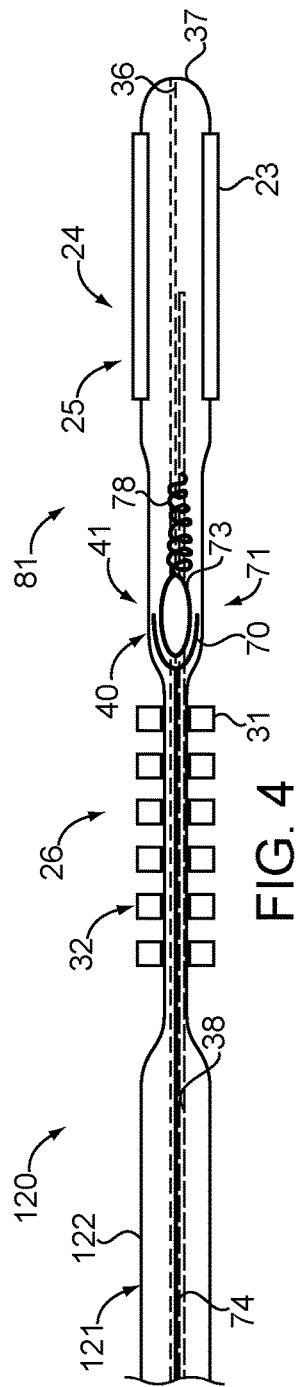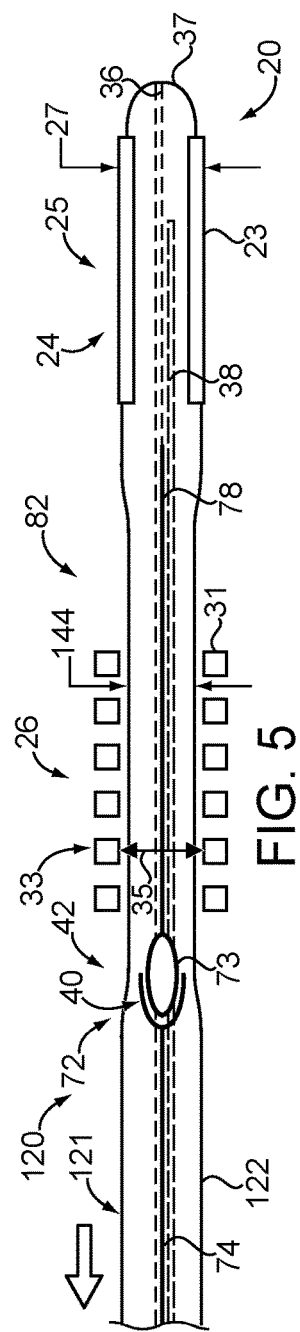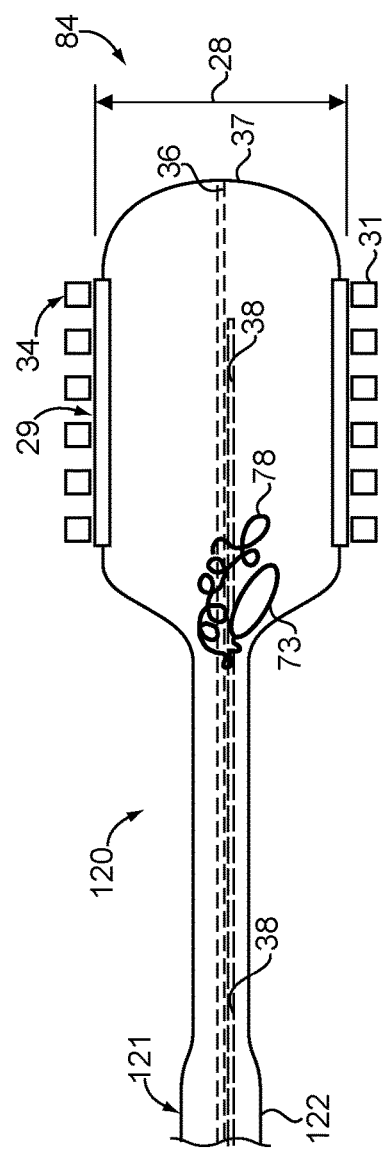

LOW PROFILE STENT DELIVERY SYSTEM AND METHOD

TECHNICAL FIELD

The present disclosure relates generally to placement of balloon expanded stents via inflation of a balloon, and more particularly to a low profile structure in which the stent is initially crimped at a location separated from the main balloon of the balloon catheter.

BACKGROUND

Stent delivery systems that utilize a balloon expandable stent mounted about a balloon have seen considerable success for many years. However, the practical limitations prevent typical balloon expanded stent structures from being manufactured to fit through low profile sheaths (such as seven French or less) to deliver stents to small diameter passageways. These structural limitations are due to practical limitations in producing small diameter catheters, practical limitations in balloon structures, and limitations in outer diameter of balloon expandable stents in a crimped state. These problems are complicated by the fact that these limitations are stacked in a typical structure in which the stent is mounted in a crimped state on a folded deflated balloon. Thus, without resorting to untested exotic materials, there are practical limits as to the outer diameter of the stent deployment system due to the limitations on how small the diameter can be made to be where the stent is crimped about the deflated balloon.

The present disclosure is directed toward one or more of the problems set forth above.

SUMMARY

In one aspect, a low profile stent delivery system includes a balloon catheter with a balloon mounted about a catheter at a first location along a length of the catheter. A balloon expandable stent is crimped about the catheter at a second location that is separated from the first location. An auxiliary expander is movable with respect to the stent between a first configuration and a second configuration. The stent expands from a crimped state to a less than fully expanded state responsive to movement of the auxiliary expander from the first configuration to the second configuration. An inner diameter of the stent in the less than fully expanded stent is greater than an outer diameter of the balloon in a deflated state.

In another aspect, a low profile stent delivery system includes a balloon catheter that includes a catheter and a balloon mounted about the catheter at a first location along its length. The low profile stent delivery system has a first configuration characterized by a balloon expandable stent being crimped about the catheter at a second location that is separated from the first location. The system has a second configuration characterized by the balloon expandable stent being in a less than fully expanded state at the second location. The inner diameter of the stent in less than fully expanded state is greater than an outer of the balloon in a deflated state. The system has a third configuration characterized by the balloon expanded stent being in the less than fully expanded state at the first location. The delivery system as a fourth configuration characterized by the balloon expandable stent being in a fully expanded state at the first location in contact with the balloon.

In another aspect, a method for delivering a balloon expandable stent to a treatment location includes positioning a sheath that is seven French or less in a passageway. A low profile stent delivery system is slid through the sheath. A balloon expandable stent of the low profile stent delivery system is expanded from a crimped state to a less than fully expanded state. A balloon of the low profile stent delivery system is moved with respect to the stent to a position within the less than fully expanded stent. The stent is expanded from the less than fully expanded state to a fully expanded state at the treatment site by inflating the balloon.

BRIEF DESCRIPTION OF THE DRAWINGS

FIG. 1 is a partial side diagrammatic view of a low profile stent delivery system in a first configuration;

FIG. 2 is a partial side diagrammatic view of the low profile stent delivery system of FIG. 1 in a second configuration;

FIG. 3 is a partial side diagrammatic view of the stent delivery system of FIGS. 1 and 2 in a fourth configuration;

FIG. 4 is a partial side diagrammatic view of a low profile stent delivery system according to another embodiment in a first configuration;

FIG. 5 is a partial side diagrammatic view of the stent delivery system of FIG. 4 in a second configuration;

FIG. 6 is a partial side diagrammatic view of the stent delivery system of FIGS. 4 and 5 in a fourth configuration;

DETAILED DESCRIPTION

Figure 7:
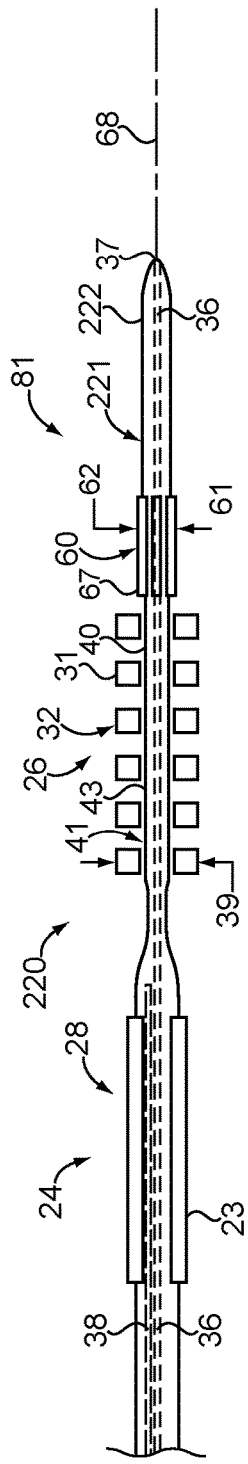
FIG. 7 is a partial side diagrammatic view of a low profile stent delivery system according to still another embodiment in a first configuration.

Referring initially to FIGS. 1-3, a low profile stent delivery system 20 includes a balloon catheter 21 that includes a catheter 22 and a balloon 23 mounted about the catheter at a first location 24 along a length of the catheter. A balloon expandable stent 31 is crimped about the catheter at a second location 26 that is separated from the first location 24. A balloon expandable stent according to the present disclosure means a stent that is plastically expanded, which is not a self expanding stent that is biased toward an expanded state. An auxiliary expander 40 is movable with respect to the stent 31 between a first configuration 41 as showing FIG. 1 and a second configuration 42 as shown in FIG. 2. In this embodiment, balloon 23 can be considered a main balloon, and the auxiliary expander 40 includes an auxiliary balloon 43 mounted about the catheter 22 at the second location 26. The auxiliary balloon 43 is deflated in the first configuration 41 and inflated in the second configuration 42. Catheter 22 may have a reduced diameter in the region of location 26 relative to a diameter at location 24, as shown. Auxiliary balloon 43 may comprise a suitable medical balloon known in the art, but may preferably comprise a non-compliant balloon, which may or may not be mounted about a reduce diameter section of catheter 22 as shown in FIG. 1. The stent 31 expands from a crimped state 32, as shown in FIG. 1 to a less than fully expanded state 33 as shown in FIG. 2 responsive to movement of the auxiliary expander 40 from the first configuration 41 (auxiliary balloon 43 un-inflated) to the second configuration 42 (auxiliary balloon 43 inflated). An inner diameter 35 of the stent 31 in the less than fully expanded state 33 is greater than an outer diameter 27 of the main balloon 23 in a deflated state 25. By locating the crimped stent 31 away from the main balloon 23, the overall profile of the stent delivery system 20 can be reduced because the radial thicknesses of the main balloon 23 and the crimped stent 31 are no longer stacked upon one another as in typical prior art balloon expanded stent delivery systems. Those skilled in the art will appreciate that maybe the biggest driver in reducing profile is the outer diameter of the stent 31 in the crimped state 32. Thus, in most instances of a low profile stent delivery system 20 according to the present disclosure, the outer diameter of the stent 31 in the crimped state 32 will be equal to or greater than an outer diameter of the main balloon 23 in its deflated state 25 as shown in FIGS. 1 and 2. Although not readily apparent in FIGS. 1 and 2, those skilled in the art will appreciate that main balloon 23 will likely be folded in a manner well known in the art when in its deflated state 25. Although not necessary, the auxiliary balloon 43 will likely have the same or less compliance relative to main balloon 23.

After the auxiliary balloon 43 has expanded stent 31 to its less than fully expanded state 33 as shown in FIG. 2, the auxiliary balloon 43 may be deflated and the balloon catheter 21 maneuvered to position the main balloon 23 within the stent 31. Thereafter, the main balloon 23 may be inflated as shown in FIG. 3 to change the stent 31 from the less than fully expanded state 33 to a fully expanded state 34 as shown in FIG. 3. Of note is the fact that the outer diameter 28 of the main balloon 23 in an inflated state 29 is greater than an outer diameter 44 of the auxiliary balloon 43 in an inflated state 45. Although not necessary, balloon catheter 21 may define a wire guide lumen 36 that opens through a distal end 37 of catheter 22. Although utilizing the wire guide lumen 36 as also an inflation lumen for one or both of the main balloon 23 and auxiliary balloon 43 is within the scope of this disclosure, the illustrated embodiment is shown as including a separate inflation lumen 38 that is defined by catheter 22. Both main balloon 23 and auxiliary balloon 43 may share the common inflation lumen 38.

In the illustrated embodiment, a rupture disk 54 may be positioned to block the inflation lumen 38 between the first location 24 corresponding to main balloon 23 and the second location 26 corresponding to auxiliary balloon 43. The auxiliary balloon 43 may be configured to move from the un-inflated first configuration 41 to the inflated second configuration 42 responsive to a first inflation pressure in the inflation lumen 38. The ruptured disk 54 may be configured to rupture at a rupture pressure that is greater than the first inflation pressure. The main balloon 23 is constructed to move from the deflated state 28 to the inflated state 29 responsive to a second inflation pressure that is equal to or greater than the rupture pressure associated with rupture disk 54. By allowing the thickness dimensions of the stent 31 and main balloon 23 to not be stacked, the low profile stent delivery system 20 is constructed to be slidably received through a sheath that is seven French or less. This enables the stent delivery system 20 to deliver a stent 31 to peripheral small diameter blood vessels previously unreachable with larger diameter conventional stent delivery systems.

Referring now to FIGS. 4-6, a second embodiment of a low profile stent delivery system 120 differs from the previous embodiment in that the auxiliary expander 40 includes a wedge 70, as opposed to the auxiliary balloon 43 of the previous embodiment. Otherwise, several of the features of this embodiment include identical numbers because they represent similar features as the first embodiment. Low profile stent delivery system 120 includes a balloon catheter 121 that includes a catheter 122 and a balloon 23 mounted about the catheter 122 at a first location 24 along the length of the catheter. Like the previous embodiment, a balloon expandable stent 31 is crimped about the catheter 122 at a second location 26 that is separated from the first location 24. The auxiliary expander, which includes wedge 70 is movable with respect to the stent 31 between a first configuration 41 as shown in FIG. 4 to a second configuration 42 as shown in FIG. 5. In particular, wedge 70 may be positioned within catheter 122 and be movable from a first position 71 to a second position 72. In this embodiment, first position 71 is distal to the second location 26, and second position 72 is proximal to the second location 26. Thus, in this embodiment, wedge 70 is connected to a tether 74 that allows the user to pull the wedge 70 from the first position 71 to the second position 72. Movement of wedge 70 occurs responsive to tension in tether 74. In an alternative embodiment, not shown, the wedge could be initially positioned proximal to the second location 26 and be pushed to a second location distal of the second location 26 responsive to advancement of a compression member coupled to wedge 70 in a distal direction. Although not necessary, both wedge 70 and tether 74 may be positioned in inflation lumen 38, which is the means by which main balloon 23 is inflated.

Wedge 70 may be flexible between a larger profile as shown due to the inclusion of a wedge opener 73. Wedge opener 73 may be connected to a separate tether 78 that is configured to cause the wedge opener 73 to detach from wedge 70 after wedge 70 has been moved to the second position 72. For instance, the connection between wedge 70 and wedge opener 73 maybe engineered to be weak relative to the expected tension in tether 74 when wedge 70 is withdrawn proximally away from stent 31. After becoming disconnected as shown in FIG. 6, the wedge opener 73 and its associated tether 78 are no longer useful and may remain inside or near main balloon 23. At the same time, wedge 70 may collapse and be withdrawn in a proximal direction from stent delivery system 120 so that it does not present an obstacle to inflation of main balloon 23 via inflation lumen 38. Thus, the connection between the wedge 70 and the wedge opener 73 may be weak such that sufficient tension in tether 74 will break that connection and detach the opener 73 from wedge 70. This detachment permits the wedge 70 to collapse to a low profile for travel through a catheter lumen, which may be the inflation lumen 38 as shown.

In one example variation, the wedge 70 may itself be a small balloon that is inflated via a passageway in tether 74. In such as case, the wedge balloon would be deflated after being pulled through the stent 31. Alternatively, the wedge 70 may be made from a porous material that permits inflation of main balloon 23 without removal of wedge 70 from catheter 122. In still another version, the wedge 70 may be made to include a non-Newtonian fluid/material that changes properties based on forces applied to it. In still another version, the wedge 70 could be made from a dissolvable material, and a solvent may be introduced via the inflation lumen 38 after the wedge 70 has moved stent 31 to its less than fully expanded configuration as shown in FIG. 5. Like the earlier embodiment, movement of wedge 70 from the first position 71 to the second position 72 causes the stent 31 to expand from a crimped state 32 to a less fully expanded state 33. Thereafter, catheter 122 can be maneuvered with main balloon 23 deflated to position the main balloon within the less than fully expanded stent 31. Thereafter, the main balloon 23 can be inflated as shown in FIG. 6 to expand the stent 31 to a fully expanded state 34.

Figure 8:
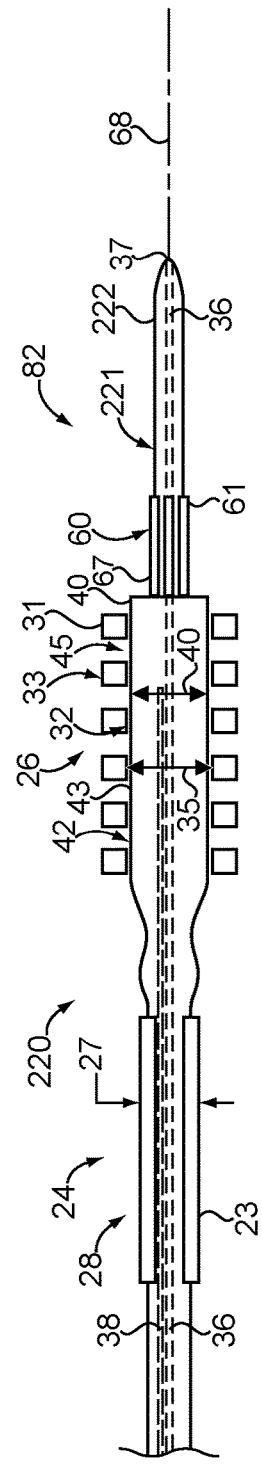
FIG. 8 is a partial side diagrammatic view of the stent delivery system of FIG. 7 in a second configuration.
Figure 9:
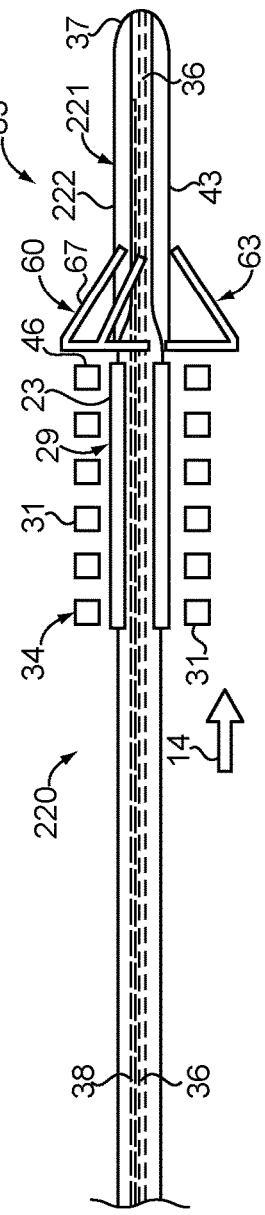
FIG. 9 is a partial side diagrammatic view of the stent delivery system of FIGS. 7 and 8 in a third configuration.
Figure 10:
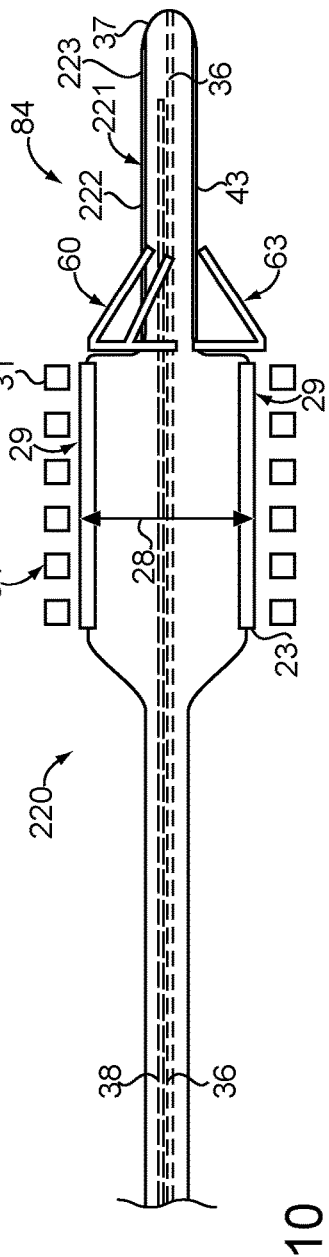
FIG. 10 is a partial side diagrammatic view of the stent delivery system of FIGS. 7-9 in a fourth configuration.

Referring now in addition to FIGS. 7-10, still another embodiment of a low profile stent delivery system 220 is illustrated. This embodiment shares some similarities with the first two embodiments, and like features include the same numbering system. However, this embodiment differs from the earlier embodiments by the reverse locations of the main balloon 23 and the auxiliary balloon 43. This embodiment also differs by the inclusion of a stent securement mechanism 60. Nevertheless, those skilled in the art will appreciate that the delivery systems 20 and 120 described previously could also include a stent securement mechanism 60 as described infra. Where the same numbers are used as per the previously described embodiments, the earlier description using those numbers also applies. The stent securement mechanism 60 is mounted to catheter 222 of balloon catheter 221, and is movable from an inactive configuration 61 as shown in FIGS. 7 and 8 to an active configuration 63 as shown in FIGS. 9 and 10. The function of the stent securement mechanism 60 is to help prevent stent 31 in its less than fully expanded state 33 from sliding out of place when the balloon catheter 21 is maneuvered between FIGS. 8 and 9 to position the main balloon 23 within the less than fully expanded stent 31. This strategy permits the stent 31 to be expanded from its crimped state 32 to its less than fully expanded state 33 at the location where the stent 31 will eventually be fully expanded. In the inactive configuration 61, the stent securement mechanism 60 may have an outer diameter 62 that is less than an outer diameter 39 of the stent 31 in its crimped state 32. In the active configuration 63, the stent securement mechanism 60 is positioned to contact a distal end 46 of stent 31 when the stent 31 is in the less than fully expanded state 33.

In this illustrated embodiment, the stent securement mechanism 60 includes a plurality of stent securement arms 67 that are parallel to a longitudinal axis 68 in the inactive configuration 61. When changed to the active configuration, the stent securement arms 67 may deform, change shape or pivot about a mid-point (as shown) in order to inhibit migration of stent 31 prior to stent 31 being fully expanded as shown in FIG. 10. In this embodiment, balloon catheter 221 may include one or more radiopaque markers that could be used to help the user to confirm when the system 220 has been moved from the configuration of FIG. 8 into the configuration of FIG. 9. One could expect the outer diameter 62 of the stent securement mechanism to increase responsive to the change from the inactive configuration 61 to the active configuration 63. When this is done, the deflated auxiliary balloon 43 may be maneuvered into a hollow distal nose segment 223 of catheter 222. Like the embodiment of FIGS. 1-3, both main balloon 23 and auxiliary balloon 43 may share a common inflation lumen 38, that is separate from a wire guide lumen 36, if included. The other embodiments could also include appropriate markers to assist the user in confirming proper placement of the stent 31 and other features of the balloon catheter during delivery.

Figure 11:
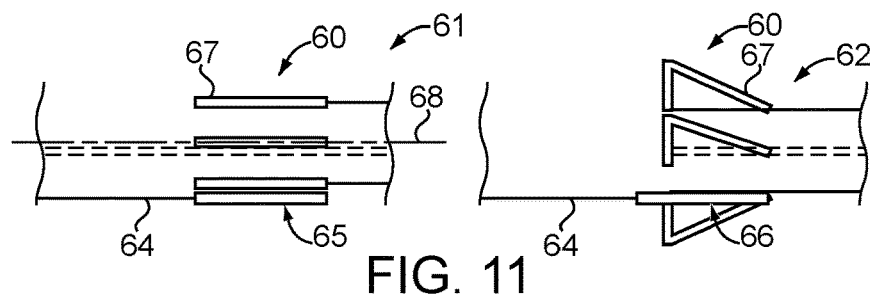
FIG. 11 is a schematic view of a stent securement mechanism for the embodiment of the FIGS. 7-10 in an inactive configuration and an active configuration.
Figure 12:
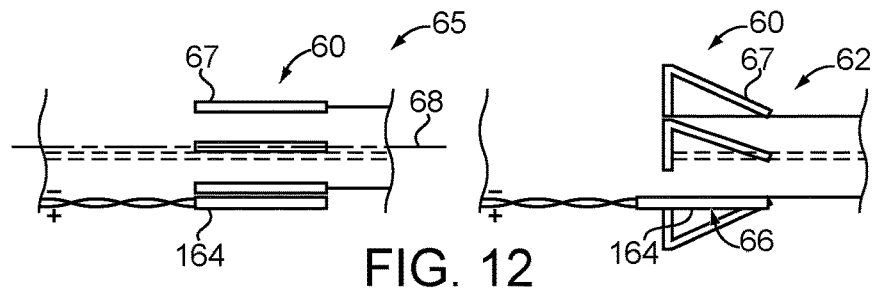
FIG. 12 is a schematic view of another version of a stent securement mechanism in an inactive configuration and an active configuration.
Figure 13:
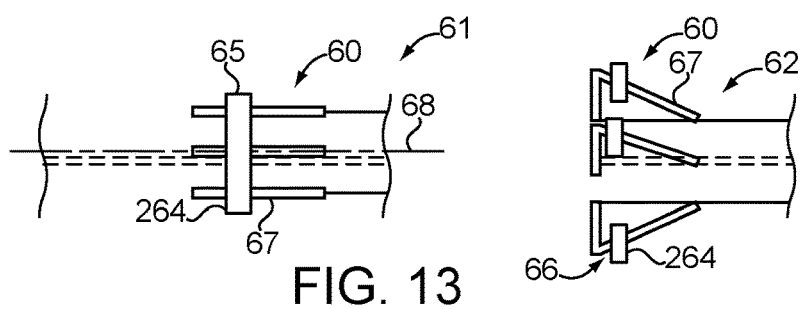
FIG. 13 is a schematic view of still another stent securement mechanism in an inactive configuration and an active configuration.

Referring now in addition to FIGS. 11-13, movement of the stent securement arms 67 of stent securement mechanism 60 from the inactive configuration 61 to the active configuration 63 may be achieved by the inclusion of a deployment actuator 64 that is in contact with the stent securement mechanism 60. In the version shown in FIG. 11, the deployment actuator 64 may comprise a wire that is connected to the stent securement arms 67, and causes the stent securement arms to move from the inactive configuration 61 to the active configuration 63 responsive to the deployment actuator wire 64 being pulled by the user from first position 65 to a second position 66. Thus, the stent securement mechanism 60 moves from the inactive configuration 61 to the active configuration 63 responsive to movement of the deployment actuator 64 from the first position 65 to the second position 66. In the version of FIG. 12, the deployment actuator 164 may comprise an electrically responsive wire that changes in length responsive to a current supplied to the deployment actuator wire 164. In this embodiment, application of current causes the deployment actuator wire 164 to shorten in response to the electric current to move the stent securement arms 67 to the active configuration 63. FIG. 13 shows still another alternative strategy in which the stent securement arms 67 are biased toward the active configuration 63 but are held in the inactive configuration 61 by a deployment actuator 264 in the form of a rupture band. Preferably, in each of the embodiments that include a stent securement mechanism 60 that includes a plurality of stent securement arms 67, the stent securement arms 67 are preferably parallel to the longitudinal axis 68 of the catheter 222 when in the inactive configuration 61 as shown.

Figure 14:
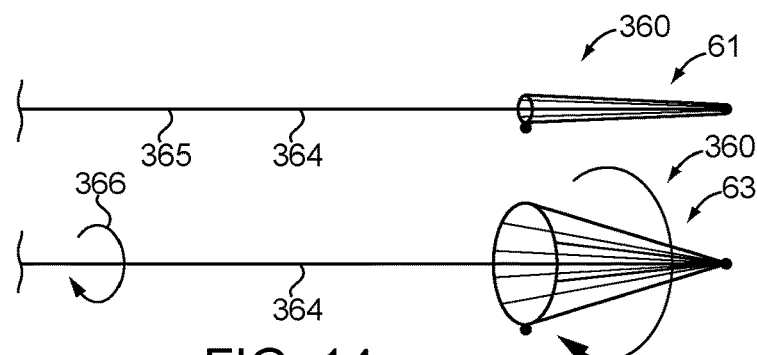
FIG. 14 shows still another stent securement mechanism in both an inactive configuration and an active configuration.
Figure 15:
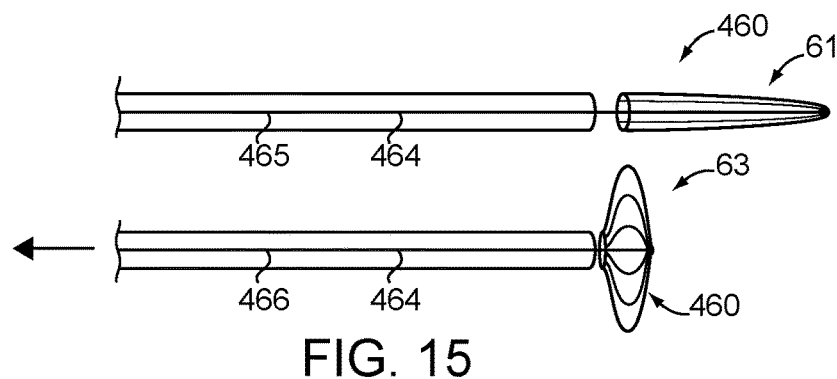
FIG. 15 is a schematic view of still another stent securement mechanism shown in both its inactive configuration and active configuration.

Referring now to FIGS. 14 and 15, a couple of alternative strategies are shown for a stent securement mechanism that does not includes the stent securement arms 67 of the previous embodiments. In particular, in FIG. 14, stent securement mechanism 360 includes a deployment actuator 364 that is maneuvered by rotation about its longitudinal axis from first position 365 to second position 366 to deploy the stent securement mechanism 360 from an inactive configuration 61 that is generally parallel to the longitudinal axis to a larger diameter in the active configuration 63. In the embodiment of FIG. 15, a stent securement mechanism 460 includes a deployment actuator wire 464 that is moved from a first position 465 corresponding to an inactive configuration 61 in a proximal direction to a second position 466 in which the stent securement mechanism 460 presents a larger diameter in its active configuration 63. For example, the stent securement mechanism 460 may comprise a wire mesh that is relaxed and at a low profile when the inner mandrel is extended, but bunches up to a larger profile in the active configuration when retracted against the less than fully expanded stent 31. In other versions, not shown, the stent securement mechanism maybe smaller than the inner diameter of stent 31 in the less than fully expanded state 33, but the surface of the stent securement mechanism may be rough to prevent stent migration. In still another alternative, which is not shown, the stent securement mechanism 60 may comprise a small balloon positioned just distal of stent 31, which is deflated in the inactive configuration 61 but inflated in the active configuration 63.

Referring now to all of the low profile stent delivery systems 20, 120, 220 illustrated previously. In all cases, the delivery system includes a balloon catheter 21, 121, 221 that includes a catheter 22, 122, 222 and a balloon 23 mounted about the catheter at a first location 24 along the length of the catheter. All embodiments also include a balloon expandable stent 31 that is changed from a crimped configuration 32 to a less than fully expanded configuration 33 and finally to a fully expanded configuration 34. All versions of the system 20, 120, 220 have a first configuration 81 (FIGS. 1, 4 and 7) characterized by the balloon expandable stent 31 being crimped about the catheter 22, 122, 222 at the second location 26 that is separated from the first location 24. The low profile stent system 20, 120, 220 has a second configuration 82 (FIGS. 2, 5, and 8) characterized by the balloon expandable stent 31 being in a less than fully expanded state 33 at the second location 26. The inner diameter 35 of the stent 31 of the less than fully expanded state 33 is greater than an outer diameter 27 of the main balloon 23 in its deflated state 28. The low profile stent delivery system 20, 120, 220 may be changed to a third configuration 83 (FIG. 9) that is characterized by the balloon expandable stent 31 being in the less than fully expanded state 33 at the first location 24 corresponding to the main balloon 23. This configuration is omitted from the embodiments of FIGS. 1-6 but is shown in FIG. 9 with regard to that embodiment. The low profile stent delivery system 20, 120, 220 can also be changed to a fourth configuration 84 (FIGS. 3, 6 and 10) that is characterized by the balloon expandable stent 31 being in a fully expanded state 34 at the first location 24 in contact with the main balloon 23.

The change from the first configuration 81 to the second configuration 82 may be done responsive to movement of the auxiliary expander 40 with respect to the stent 31. The change from the second configuration 82 to the third configuration 83 may be done responsive to movement of the balloon 23 with respect to the stent 31 along the axis 68 of catheter 22, 122, 222. Finally, the change from the third configuration 83 to the fourth configuration 84 may be accomplished responsive to inflation of the main balloon 23.

INDUSTRIAL APPLICABILITY

The present disclosure finds generally applicability in any balloon expanded stent delivery application. The present disclosure finds particular application in low profile balloon expandable stent delivery systems. Finally, the present disclosure finds specific applicability to low profile stent delivery systems that can be slidably received through a sheath that is seven French or less for reaching and placing stents in hard to reach small diameter blood vessels previously unreachable with conventional stent delivery system technology.

Figure 16:
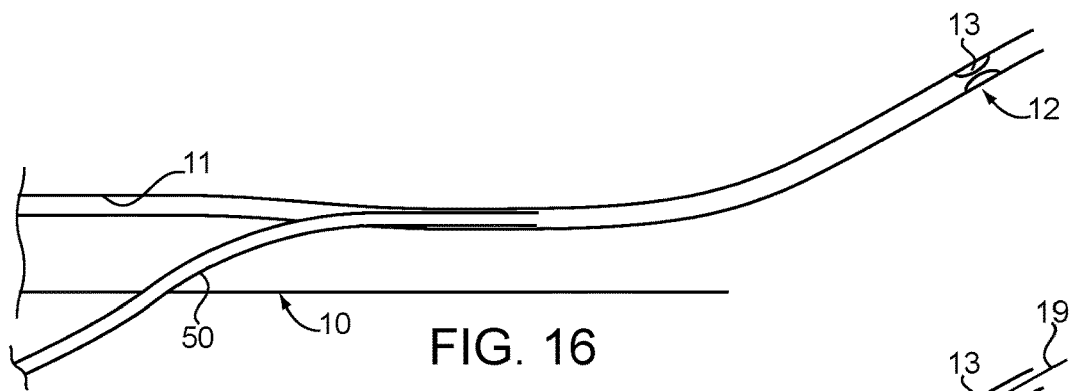
FIG. 16 is a schematic view of a sheath positioned in a passageway according to a method of the present disclosure.
Figure 17:
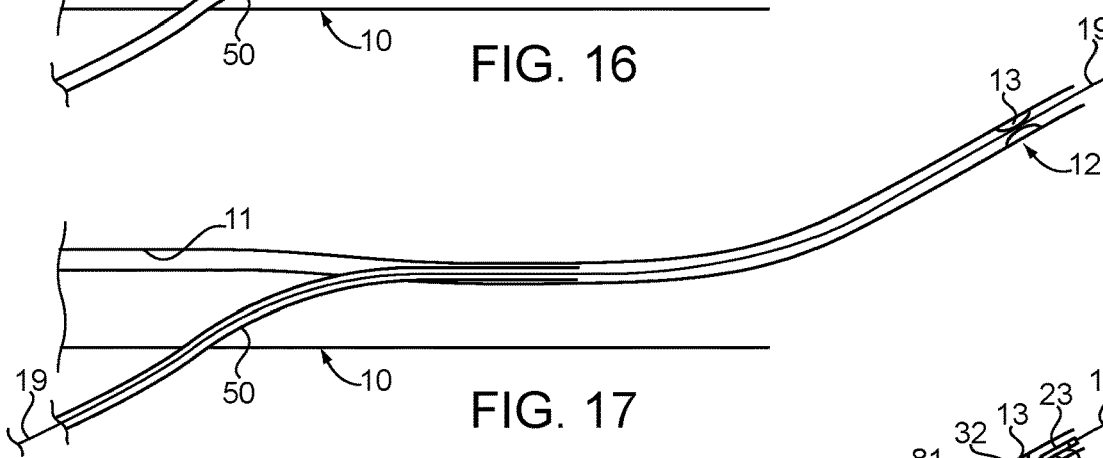
FIG. 17 shows the method of FIG. 16 after a wire guide has been positioned with respect to a treatment location.
Figure 18:
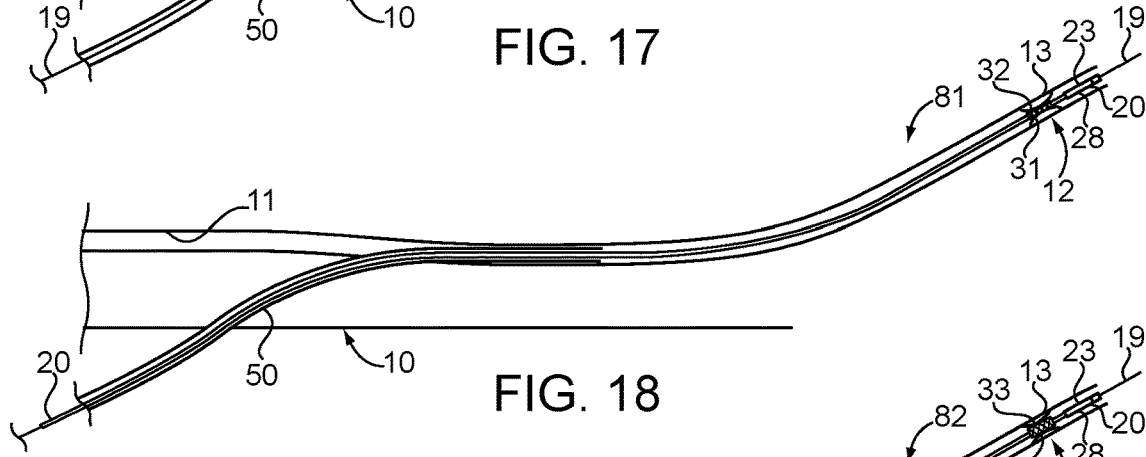
FIG. 18 shows the method after a low profile stent delivery system according to the present invention has been slid through the sheath along the wire guide to the treatment location in a first configuration.
Figure 19:
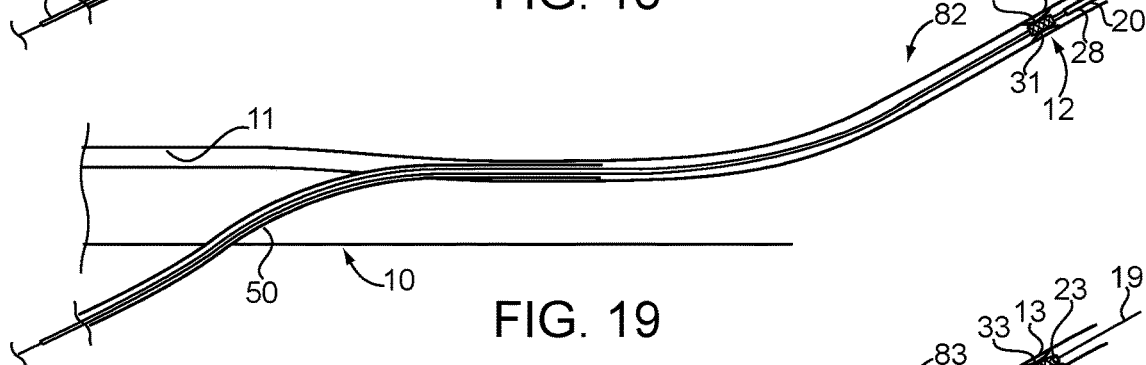
FIG. 19 shows the low profile stent delivery system of FIG. 18 in a second configuration.
Figure 20:
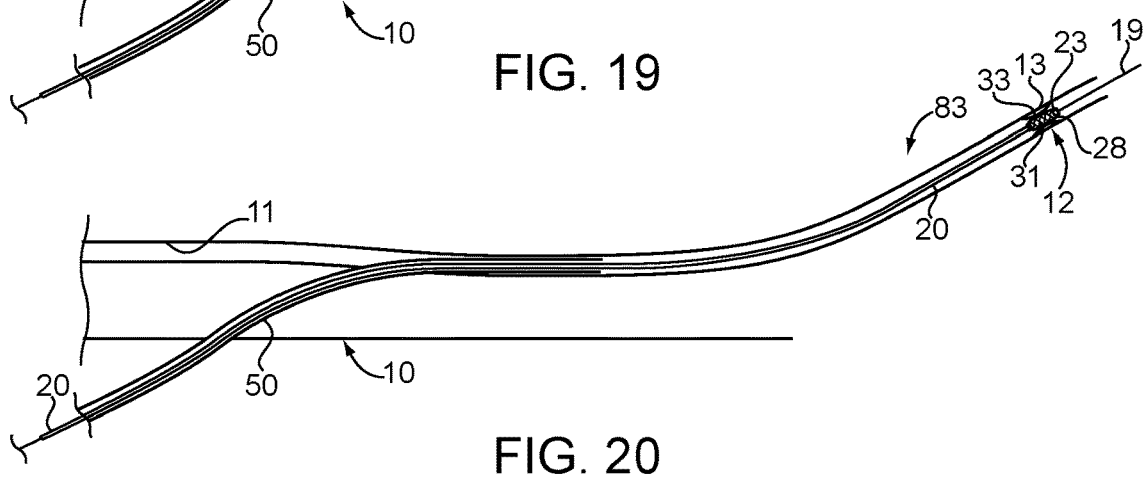
FIG. 20 shows the low profile stent delivery system in a third configuration.
Figure 21:
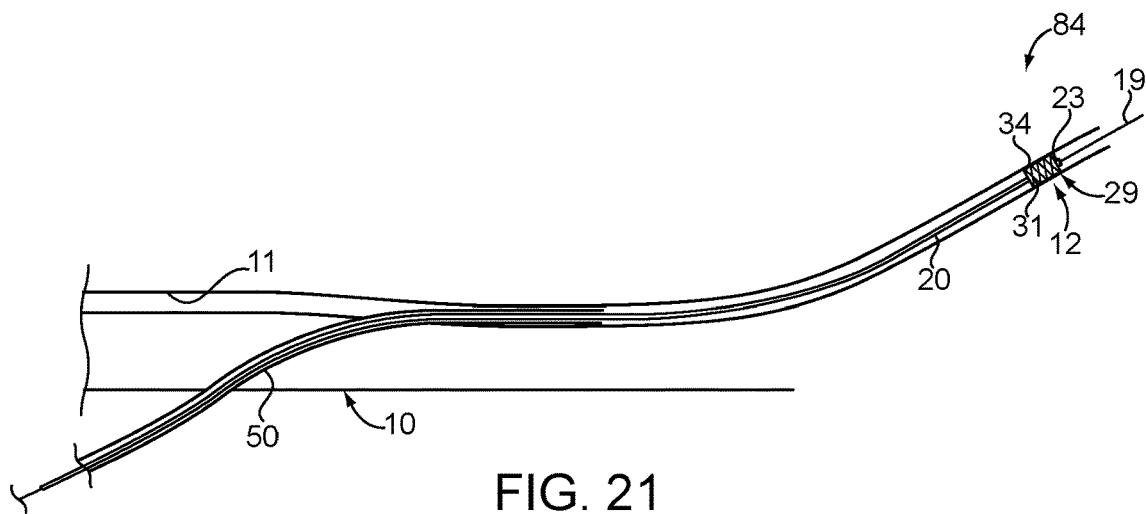
FIG. 21 shows the stent delivery system in a fourth configuration.
Figure 22:
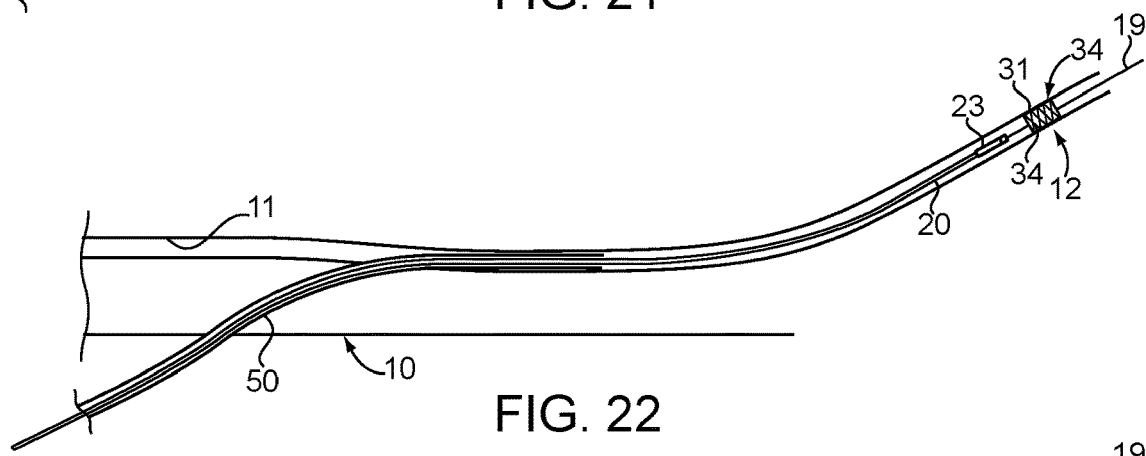
FIG. 22 shows the low profile stent delivery system being withdrawn from the treatment location leaving a fully expanded stent in place.
Figure 23:
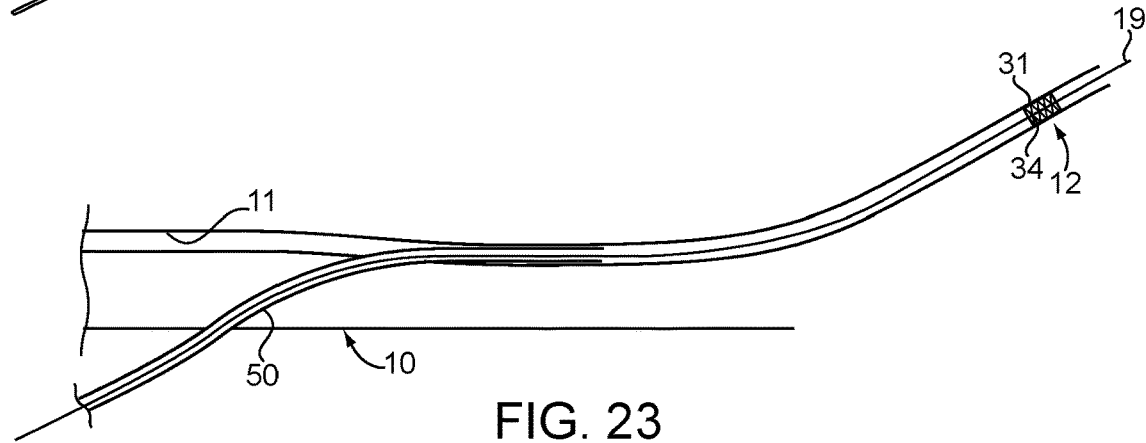
FIG. 23 shows the fully expanded stent in place at the treatment location after the stent delivery system has been withdrawn from the sheath.
Figure 24:
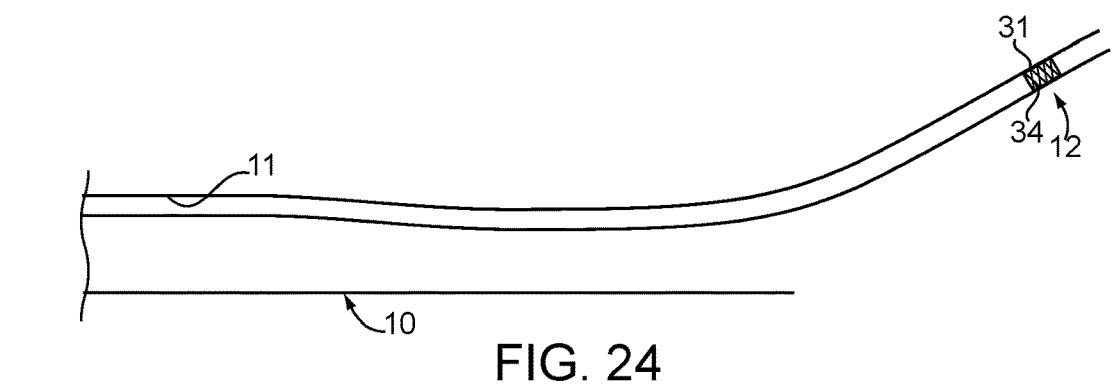
FIG. 24 is a schematic view showing the fully expanded stent in location at the treatment location after withdrawal of both the sheath and wire guide from the body.

Referring now in addition to FIGS. 16-24, a method of delivering a balloon expandable stent 31 to a treatment location 12 is illustrated. Treatment location 12 may be an occlusion 13 needing to be stented in a small diameter blood vessel of a live body 10. Alternatively, body 10 and the associated passageway 11 may be artificial such as for teaching or demonstration purposes. In any event, a sheath 50 that is seven French or less is positioned in a passageway 11 as shown in FIG. 16. Next, a wire guide 19 may be maneuvered through sheath 50 through the passageway 11 to an occlusion 13 at treatment location 12. As shown in FIG. 17, thereafter, the low profile stent delivery system according to any of the embodiment may be passed over wire guide 19 to the treatment location 12. In these illustrations, the first embodiment of the low profile stent delivery system 20 is illustrated. The low profile stent delivery system 20 is slid through sheath 50 to position the stent 31 in its crimped state 32 in the occlusion 13 with the system 20 in its first configuration 81 as described earlier. Next, the stent delivery system 20 is changed to the second configuration 82 by changing the auxiliary expander 40 from its first configuration 41 to its second configuration 42 by inflating auxiliary balloon 43. In changing from FIG. 19 to FIG. 20, the stent delivery system 20 is changed from its second configuration 82 to its third configuration 83 by positioning the main balloon 23 within the less than fully expanded stent 31. Next, the system 20 is changed from the third configuration 83 to the fourth configuration 84 as shown in FIG. 21 by inflating main balloon 23 to expand stent 31 to its fully expanded state 34 to open the occlusion 13. Thereafter, the stent delivery system 20 may be maneuvered away from the treatment site 12 as shown in FIG. 22 and eventually withdrawn completely from the body 10 as shown in FIG. 23. Thereafter, the wire guide 19 and the small diameter sheath 50 may be withdrawn from the body 10 as shown in FIG. 24, leaving the stent 31 in its fully expanded state 34 at the treatment location 12.

Returning to FIG. 18, the balloon expandable stent 31 is expanded from the crimped state 32 to the less than fully expanded state 33. Next, when changing from the second configuration 82 to the third configuration 83 of FIG. 20, the balloon 23 is moved with respect to stent 31 to a position within the less than fully expanded stent 31. Thereafter, the stent 31 is changed from its less than fully expanded state 33 to its fully expanded state 34 at the treatment site 12 by inflating the main balloon 23 as shown in FIG. 21.

In all of the embodiments, the step of expanding the balloon expandable stent 31 to the less than fully expanded state 33 is accomplished by moving the auxiliary expander 40 from its first configuration 41 to its second configuration 42. In the embodiment shown, the balloon 23 is moved in a proximal to distal direction 14 when changing from the second configuration 82 as shown in FIG. 19 to the third configuration 83 as shown in FIG. 20.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A low profile stent delivery system comprising:
a balloon catheter that includes a catheter and a balloon mounted about the catheter at a first location along a length of the catheter;
a balloon expandable stent crimped about the catheter at a second location that is separated from the first location in a first arrangement;
an auxiliary expander that is movable with respect to the stent between a first configuration and a second configuration;
wherein the stent expands from a crimped state to a less than fully expanded state responsive to movement of the auxiliary expander from the first configuration to the second configuration;
wherein an inner diameter of the stent in the less than fully expanded state is greater than an outer diameter of the balloon in a deflated state; and
wherein the stent expands from the less than fully expanded state to a fully expanded state responsive to inflation of the balloon from the deflated state to an inflated state in a second arrangement;
wherein the outer diameter of the balloon in the inflated state is greater than a diameter of the auxiliary expander in the second configuration;
a sheath that is seven French or less; and
wherein the balloon catheter and the auxiliary expander are sized to be slidably received through the sheath.

2. The low profile stent delivery system of claim 1 wherein the second location is distal to the first location; and
a stent securement mechanism mounted to the catheter and being movable from an inactive configuration at which the stent securement mechanism is within an outer diameter that is less than an outer diameter of the stent in the crimped state, to an active configuration at which the stent securement mechanism is positioned to contact a distal end of the stent when the stent is in the less than fully expanded state.

3. The low profile stent delivery system of claim 2 including a deployment actuator in contact with the stent securement mechanism, and being movable from a first position to a second position; and
the stent securement mechanism moving from the inactive configuration to the active configuration responsive to movement of the deployment actuator from the first position to the second position.

4. The low profile stent delivery system of claim 3 wherein the stent securement mechanism includes a plurality of stent securement arms that are parallel to a longitudinal axis of the catheter in the inactive configuration.

5. The low profile stent delivery system of claim 1 wherein the auxiliary expander includes a wedge positioned inside the catheter and being movable from a first position that is one of proximal and distal to the second location, to a second position that is the other one of proximal and distal to the second location.

6. The low profile stent delivery system of claim 5 wherein the wedge is positioned in an inflation lumen fluidly connected to the balloon.

7. A low profile stent delivery system comprising:
a balloon catheter that includes a catheter and a balloon mounted about the catheter at a first location along a length of the catheter;
a balloon expandable stent crimped about the catheter at a second location that is separated from the first location;
an auxiliary expander that is movable with respect to the stent between a first configuration and a second configuration;
wherein the stent expands from a crimped state to a less than fully expanded state responsive to movement of the auxiliary expander from the first configuration to the second configuration;
wherein an inner diameter of the stent in the less than fully expanded state is greater than an outer diameter of the balloon in a deflated state;
wherein the balloon is a main balloon;
the auxiliary expander includes an auxiliary balloon mounted about the catheter at the second location, and being deflated in the first configuration and inflated in the second configuration;
wherein the auxiliary balloon and the main balloon share a common inflation lumen that is defined by the catheter;
an outer diameter of the main balloon in an inflated state is greater than an outer diameter of the auxiliary balloon in an inflated state;
a rupture disk blocking the inflation lumen between the first location and the second location;
the auxiliary balloon moves from the first configuration to the second configuration responsive to a first inflation pressure in the inflation lumen;
the rupture disk ruptures at a rupture pressure that is greater than the first inflation pressure; and
the main balloon is moved to the inflated state responsive to a second inflation pressure that is equal to or greater than the rupture pressure.

8. The low profile stent delivery system of claim 7 including a sheath that is seven French or less; and
wherein the balloon catheter and the auxiliary expander are sized to be slidably received through the sheath.

9. The low profile stent delivery system of claim 7 wherein the catheter defines a wire guide lumen that opens through a distal end of the catheter.

10. The low profile stent delivery system of claim 7 wherein the main balloon is positioned distally from the auxiliary balloon.

11. A low profile stent delivery system comprising:
a sheath that is seven French or less;
a balloon catheter that is slidably received in the sheath, and includes a catheter and a balloon mounted about the catheter at a first location along a length of the catheter;
a balloon expandable stent;
the low profile stent delivery system has a first configuration characterized by the balloon expandable stent being crimped about the catheter at a second location that is proximal to, and separated from, the first location;
the low profile stent delivery system has a second configuration characterized by the balloon expandable stent being in a less than fully expanded state at the second location, and wherein an inner diameter of the stent in the less than fully expanded state is greater than an outer diameter of the balloon in a deflated state;
the low profile stent delivery system has a third configuration characterized by the balloon expandable stent being in the less than fully expanded state at the first location;

the low profile stent delivery system has a fourth configuration characterized by the balloon expandable stent being in a fully expanded state at the first location in contact with the balloon; and wherein a change from the first configuration to the second configuration is responsive to movement of an auxiliary expander within and with respect to the stent.

12. The low profile stent delivery system of claim 11 including the auxiliary expander coupled to the catheter;

is responsive to movement of the auxiliary expander within and with respect to wherein a change from the second configuration to the third configuration is responsive to movement of the balloon with respect to the stent along an axis of the catheter; and wherein a change from the third configuration to the fourth configuration is responsive to inflation of the balloon.

13. The low profile stent delivery system of claim 12 wherein the balloon is a main balloon; and the auxiliary expander includes an auxiliary balloon mounted about the catheter at the second location.

14. The low profile stent delivery system of claim 12 wherein the auxiliary expander includes a wedge positioned inside the catheter and being movable from a first position that is one of proximal and distal to the second location, to a second position that is the other one of proximal and distal to the second location.

15. A low profile stent delivery system comprising:

a balloon catheter that includes a catheter and a balloon mounted about the catheter at a first location along a length of the catheter;

a balloon expandable stent crimped about the catheter at a second location that is separated from the first location in a first arrangement;

an auxiliary expander that is movable with respect to the stent between a first configuration and a second configuration;

wherein the stent expands from a crimped state to a less than fully expanded state responsive to movement of the auxiliary expander from the first configuration to the second configuration;

wherein an inner diameter of the stent in the less than fully expanded state is greater than an outer diameter of the balloon in a deflated state; and wherein the stent expands from the less than fully expanded state to a fully expanded state responsive to inflation of the balloon from the deflated state to an inflated state in a second arrangement;

wherein the balloon is a main balloon;

the auxiliary expander includes an auxiliary balloon mounted about the catheter at the second location, and being deflated in the first configuration and inflated in the second configuration;

an outer diameter of the main balloon in the inflated state is greater than an outer diameter of the auxiliary balloon in an inflated state;

the catheter defines a wire guide lumen that opens through a distal end of the catheter;

wherein the auxiliary balloon and the main balloon share a common inflation lumen that is defined by the catheter;

a rupture disk blocking the inflation lumen between the first location and the second location;

the auxiliary balloon moves from the first configuration to the second configuration responsive to a first inflation pressure in the inflation lumen;

the rupture disk ruptures at a rupture pressure that is greater than the first inflation pressure; and the main balloon is moved to the inflated state responsive to a second inflation pressure that is equal to or greater than the rupture pressure.

* * * * *